United States Patent [19]

Teubner et al.

[11] Patent Number: 4,532,367
[45] Date of Patent: Jul. 30, 1985

[54] ANTIMICROBIALLY EFFECTIVE DERIVATIVES OF PHENOL AND METHODS FOR THEIR PRODUCTION

[75] Inventors: Herbert Teubner, Wernigerode; Axel Kramer; Wolfgang Weuffen, both of Greifswald; Eberhard Schrötter, Rangsdorf; Gerhard Grübel, Jena, all of German Democratic Rep.

[73] Assignee: VEB Jenapharm, Jena, German Democratic Rep.

[21] Appl. No.: 412,851

[22] Filed: Aug. 30, 1982

[30] Foreign Application Priority Data

Jul. 8, 1981 [DD] German Democratic Rep. .............................. 2315622
Mar. 7, 1982 [DD] German Democratic Rep. .............................. 2382118

[51] Int. Cl.³ .............................................. C07C 39/14
[52] U.S. Cl. ........................................ 568/745; 568/744
[58] Field of Search ............... 568/716, 745, 746, 744; 424/289, 346, 347; 435/156

[56] References Cited

FOREIGN PATENT DOCUMENTS

| 0069374 | 1/1983 | European Pat. Off. ............ 568/745 |
| 2706747 | 9/1977 | Fed. Rep. of Germany ...... 568/745 |
| 2723909 | 12/1978 | Fed. Rep. of Germany ...... 568/745 |
| 75088 | 8/1970 | German Democratic Rep. ................... 568/745 |

OTHER PUBLICATIONS

Schroetter et al., "Chemical Abstracts", vol. 91, p. 211008a, (1979).
Proffit et al., "Chemical Abstracts", vol. 74, (1971), p. 87603y.
Teubner et al., "Chemical Abstracts", vol. 98, (1983), p. 215314.
Kramer et al., "Chemical Abstracts", vol. 88, (1978), p. 22356g.
Siegfried, "Chemical Abstracts", vol. 90, (1979), p. 121193g.

*Primary Examiner*—Werren B. Lone
*Attorney, Agent, or Firm*—Michael J. Striker

[57] ABSTRACT

A method is provided for the production of antimicrobially effective phenol derivatives according to general Formula I in which $R_1$ is bromine or chlorine, $R_2$ is methyl or ethyl, $R_3$ is hydrogen or sodium, potassium, ammonium or by alkyl with up to 10 C-atoms substituted ammonium, magnesium, calcium, barium, aluminum, tin, bismuth, copper, zinc, $R_4$ and $R_5$ are independently hydrogen, alkyl or alkoxy with up to 5 C-atoms, bromine or chlorine. The compounds are obtained by benzylation of 6-halogen- or 4-halogen-2-alkylphenol, halogenation of 2-alkyl-4-benzylphenol or -6-benzylphenol, or by alkylation of 6-halogen-4-benzylphenol or of 4-halogen-6-benzylphenol and if necessary through reaction of the product with hydroxide, alcoholate, carbonate or hydrogen carbonate of the above-mentioned metals. Water or lipid soluble effective substances are obtained which display a broad antimicrobial activity spectrum.

6 Claims, No Drawings

ANTIMICROBIALLY EFFECTIVE DERIVATIVES OF PHENOL AND METHODS FOR THEIR PRODUCTION

BACKGROUND OF THE INVENTION

The invention concerns a method for the production of antimicrobially effective, epidermally compatible compounds of the general formula I

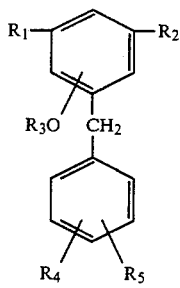

wherein
- $R_1$ is bromine or chlorine
- $R_2$ is methyl or ethyl
- $R_3$ is H, sodium, potassium, calcium, barium, ammonium, by alkyl with up to 10 C-atoms, substituted ammonium, magnesium, bismuth, tin, aluminum, zinc or copper, and
- $R_4$ and $R_5$ are independently H, alkyl or alkoxy with up to 5 C-atoms, bromine or chlorine.

Phenol derivatives, such as chlorophenol, pentachlorophenol, cresol, chlorcresol, benzylphenol, benzylchlorophenol, thymol, are known to be antiseptic and disinfecting. Disadvantages of these compounds are the to some extent high toxicity or at least poor skin compatibility and high degree of sensitization.

It is also known to produce 2-chloro-6-methyl-4-benzylphenol from 2-chloro-6-methylphenol, which arises as by-product with herbicide syntheses.

Compound 2-chloro-6-methyl-4-benzylphenol is indeed well skin-compatible and possesses in spite of a deficiency in activity generally good antimicrobial efficacy. Moreover, with 2-chloro-6-methyl-4-benzylphenol are prevented characteristic odors recognized present with the known compounds of analogous utility. Difficulties during galenical working-up can occur in several areas of use on account of the difficult water-solubility of 2-chloro-6-methyl-4-benzylphenol.

SUMMARY OF THE INVENTION

It is therefore an object of the present invention to develop methods and produce compounds, proceeding from the known good characteristics of 2-chloro-6-methyl-4-benzylphenol, which are not dependent upon the presence of by-products of herbicide syntheses and which possess characteristic odors to an as little an extent as possible.

The group of compounds satisfying these specifications should embrace not only water-soluble but also lipoidsoluble effective substances. They should display an as broad as possible antimicrobial activity spectrum with higher effectiveness.

These objects are attained according to the present invention by proceeding from 2-alkylphenol and through halogenation according to known methods, producing 2-halogen-6-alkylphenol, which latter is converted into compounds of the general formula II with $R_3 =$ H through Friedel-Crafts benzylation and if necessary transforming these into salts of the general Formula II, in which $R_3$ is sodium, potassium, calcium, barium, ammonium or by alkyl with up to 10 C-atoms, substituted ammonium, magnesium, bismuth, tin, zinc, aluminum or copper.

For production of the 6-halogen-2-alkylphenol the 2-alkylphenol is in expedient manner sulfonated in the 4-position, whereby selective (in the o-position) halogenation can proceed. Subsequently the sulfonic acid residue is hydrolytically removed.

For Friedel-Crafts benzylation the 6-halogen-2-alkylphenol is heated in the presence of Friedel-Crafts catalysts with benzyl chloride or -alcohol, if necessary with the use of an organic solvent. In addition to unsubstituted benzyl chloride or -alcohol, also those substituted by alkyl with up to 5 C-atoms or by halogen come into question.

The object of the present invention is also attained by likewise proceeding from 2-alkylphenol, which in known manner is halogenated in the 4-position and reacting the 4-halogen-2-alkylphenol, likewise in known manner, into compounds of the general Formula III with $R_3 =$H through Friedel-Crafts benzylation and, if necessary, transforming these into salts of the general Formula III, in which $R_3$ is then sodium potassium, calcium, barium, ammonium or by alkyl with up to 10 C-atoms, substituted ammonium, magnesium, bismuth, tin, zinc, aluminum or copper.

The Friedel-Crafts benzylation can be performed with unsubstituted benzyl halogenides or -alcohols or with benzyl halogenides or -alcohols substituted preferably in the p-position by alkyl with up to 5 C-atoms or by halogen.

The production of the mentioned metal salts follows by reaction of the compounds of general Formula I, in particular compounds of the general Formulas II and III, in which $R_3$ is hydrogen, with alkali or earth alkali hydroxides, with the corresponding metal alcoholates, -carbonates, -hydrogen carbonates in aqueous medium or using organic solvent. For the production of the salt, operating under from inert gas or up to even oxygen excess have been shown to be expedient in order to obtain stable colorless products.

Further possibilities for the production of the 6-halogen-2-alkyl-4-benzylphenol according to general Formula II include halogenation of 2-alkyl-4-benzylphenol as well as alkylation of 6-halogen-4-benzylphenol.

The production of the 2-alkyl-4-halogen-6-benzylphenol according to general Formula III can likewise follow through halogenation of 2-alkyl-6-benzylphenol in the 4-position as well as through alkylation of 4-halogen-6-benzylphenol in the 2-position.

The products produced according to the present invention distinguish by high antimicrobial effectiveness connected with low toxicity and good skin compatibility. In connection therewith the bromine compounds display substantially less characteristic odor than the corresponding chlorine compounds. It has furthermore been shown that the antimicrobial effectiveness of the bromine compounds exceeds that of the chlorine compounds and that the salts are nearly odorless in comparison to the free phenols.

The calcium salt, by way of example, of the 2-chloro-6-methyl-4-benzylphenol is particularly effective against gram-positive bacteria, whereas against gram-negative bacteria a microbiostatic concentration limit of 1:250 has been determined. In practice, based upon the good compatibility, a use concentration up to 1% is sufficient.

According to provided purpose of use within the art or for pharmaceutical purposes the compounds according to general Formula I can be used as oily liquids poorly soluble in water or in the form of their hydrophilic salt.

The novel features which are considered characteristic for the invention are set forth in particular in the appended claims. The invention itself, however, both as to its composition and its method of use, together with additional objects and advantages thereof, will be best understood from the following description of specific embodiments.

DESCRIPTION OF THE PREFERRED EMBODIMENTS

EXAMPLE 1

6-bromo-2-methyl-4-benzylphenol 54 g (0.5 mol) 2-methylphenol (o-cresol) are provided in a 250 ml three-necked flask fitted with stirrer, interior thermometer, Claysen mount, cooler and drying tube at room temperature. 61.0 g concentrated $H_2SO_4$ with 10% free $SO_3$ are added dropwise within 35 minutes under stirring. Upon formation of the 4-sulfonic acid of the phenol a strong exothermia is noticeable. For completion of the reaction the reaction mixture is subsequently after-stirred yet 5 hours at 80° C. After cooling the reaction mixture is sprinkled into 900 ml ice water.

After melting, the flask contents are all placed in an appropriately larger flask and then 80 g bromine (0.5 mol) are added dropwise thereto within 1½ hours at 15° to 27° C. Towards the end of the bromine addition a weak HBr development is noticeable. After-stirring is then performed for 45 minutes. The entire reaction mixture is subjected to a steam distillation with superheated steam of 180° to 200° C., in order to simultaneously split off the sulfonic acid residue in the 4-position. Therewith it is easily possible, from the 2-methylphenol, to synthesize the 6-bromo-2-methylphenol, which is an oily, water-clear liquid.

500 g of the so-obtained 6-bromo-2-methylphenol, together with 10 g zinc shavings, are heated to about 100° C. Within 20 minutes 453 g benzyl chloride are added dropwise with stirring and under moisture exclusion. For a further 12 minutes the reaction mixture is heated to 150° C. It is then held a total of 5 hours at the temperature of 150° C. After cooling, the zinc is separated. The reaction product is distilled in a vacuum at 0.03 up to 0.04 Torr. 305 g 6-bromo-2-methyl-4-benzylphenol are obtained as a weakly yellowish, oily liquid, which is nearly odorless.

EXAMPLE 2

6-chloro-2-methyl-4-benzylphenol

Analogous to the procedure in Example 1, 6-chloro-2-methyl-4-benzylphenol is produced, instead of the bromination a chlorination being provided.

EXAMPLE 3

6-bromo-2-ethyl-4-benzylphenol 61 g (0.5 mol) 2-ethylphenol, easily producible from 2-ethyl aniline, and 61 g concentrated $H_2SO_4$ with 10% free $SO_3$ are used. Synthesis of the 4-sulfonic acid from the 2-ethylphenol follows analogous to the procedure in Example 1; an exothermic reaction likewise takes place.

After complete reaction the mixture is sprinkled into 900 ml ice water and, after thawing of the ice, the bromination is performed in an appropriately dimensioned flask while also therein is provided the steam distillation with the superheated steam of 180° to 200° C. for the purpose of splitting off the $SO_3H$ group. 6-bromo-2-ethylphenol remains in the collecting main, a water-clear, oily liquid; Kp 96° C./10 Torr with an estimated index $n_D^{20}$ of 1.5631.

The so-produced 6-bromo-2-ethylphenol is reacted with benzyl chloride into 6-bromo-2-ethyl-4-benzylphenol according to Example 1 under known conditions for Friedel-Crafts alkylation.

EXAMPLE 4

Production of the sodium salt of 6-chloro-2-methyl-4-benzylphenol 23.2 g (0.1 mol) of 6-chloro-2-methyl-4-benzylphenol are dissolved in 250 ml xylene and under stirring a nitrogen stream is led through the apparatus for 5 minutes in order to displace the air oxygen. Subsequently a solution of 4 g (0.1 mol) dissolved NaOH is added in a single operation. The reaction mixture is after-stirred for about 30 minutes and under stirring and further throughput of nitrogen the solvent is distilled off in a vacuum. The corresponding sodium salt of 6-chloro-2-methyl-4-benzylphenol falls out as residue.

EXAMPLE 5

Sodium salt of 6-chloro-2-methyl-4-benzylphenol 23.2 g (0.1 mol) of 6-chloro-2-methyl-4-benzylphenol are dissolved in 230 ml carbon tetrachloride. For the purpose of excluding air oxygen, nitrogen is conducted through the apparatus for 5 minutes under stirring. An aqueous solution composed of 4 g (0.1 mol) NaOH and 5 ml $H_2O$ is added all at once to this solution. At a temperature between about 20 and 30° C. the mixture is strongly stirred 1.5 hours under further nitrogen throughput in order to complete the reaction. After this period the solvent and the employed water are distillatively separated in a vacuum. For completion of the water removal from the reaction mixture, repeated suspending of the alkali salt with carbon tetrachloride and subsequent driving off of the solvent in a vacuum are performed. After 2 to 3 of such operations the alkali salt can be designated as de-watered. The resulting crystalline residue of the alkali salt of 6-chloro-2-methyl-4-benzylphenol is pre-mixed with a little carbon tetrachloride for the purpose of good sucking off. An after-washing follows with the solvent carbon tetrachloride, since solubility therein is very low.

With this procedure the corresponding sodium salt is recovered nearly quantitatively from 6-chloro-2-methyl-4-benzylphenol. A washing with diethylether is an expedient for improving the color quality. The sodium salt of 6-chloro-2-methyl-4-benzylphenol proves to be well water-soluble.

EXAMPLE 6

Production of the potassium salt of 6-chloro-2-methyl-4-benzylphenol 23.2 g (0.1 mol) of 6-chloro-2-methyl-4-benzylphenol are dissolved in 250 ml xylene. For 5 minutes nitrogen is led through this solution under stirring for the purpose of displacing the air oxygen located in the apparatus. Under further stirring and continuous nitrogen throughput a solution composed of 5.6 g (0.1 mol) KOH dissolved in 5 ml $H_2O$ are added uninterruptedly. After-stirring is performed for 30 to 60 minutes in order to complete the reaction and subsequently the solvent xylene is distilled off in a vacuum, whereby likewise a dewatering takes place since xylene is a good drawing agent. After complete driving off of the xylene the potassium salt is suspended in a little carbon tetrachloride and sucked off. After-washing can also be performed here with carbon tetrachloride or diethylether because of the low solubility of the salt therein. Solubility of the potassium salt in water is good.

Analogous to the production of the potassium salt in the solvent xylene, acetone or carbon tetrachloride can be used as solvent in which the reaction can be performed.

EXAMPLE 7

Production of the calcium salt of 6-chloro-2-methyl-4-benzylphenol 23.2 g (0.1 mol) of 2-chloro-6-methyl-4-benzylphenol are dissolved in 250 ml acetone. A nitrogen stream is led through this solution under stirring to displace the air oxygen. A suspension composed of 7.4 g (0.1 mol) Ca(OH)$_2$ and 20 ml H$_2$O is added to the solution. On account of the low solubility of calcium hydroxide in water there ensues the insertion of the doubled equivalent. The mixture is intensively stirred about 60 minutes at 20°–30° C. under continuous throughput of nitrogen within the apparatus. The acetonic solution contains the desired calcium salt of 2-chloro-6-methyl-4-benzylphenol and is separated of excess calcium hydroxide by filtration. The solvent acetone is subsequently removed under vacuum. For purpose of further dewatering of the resulting crystalline calcium salt it is suspended several times with carbon tetrachloride and solvent is separated each time in a vacuum with part of the water. The resulting calcium salt is a nearly white, very stable compound, which is however only little soluble in water.

Analogous to Examples 4–7 the alkali and earth alkali salts as well as the ammonium, bismuth, tin, zinc, aluminum and copper salts of 6-chloro-2-ethyl-4-benzylphenol can be produced.

EXAMPLE 8

2-chloro-6-methyl-4-(4'-tert. butylbenzyl)-phenol 4-tert. butylbenzyl chloride can be obtained for example by chlormethylation of tert. butylbenzene. This substituted benzene is producible by Friedel-Crafts reaction from benzene and the tert. butyl halogenide.

106.5 g (0.75 mol) 2-chloro-6-methylphenol and 45.67 g (0.25 mol) 4-tert. butylbenzyl chloride are dissolved in 200 ml chloroform, 22.5 g water-free zinc chloride are added for initiating the Friedel-Crafts reaction, and the mixture is kept 5–6 hours at 60° C. under stirring. After cooling follows a three-fold washing, each time with about 200 ml water, for dissolving out the zinc chloride from the reaction mixture. The organic phase is dried across magnesium sulfate, the solvent chloroform is driven off and subsequent in a vacuum the 2-chloro-6-methyl-4-(4'-tert. butylbenzyl)-phenol is distilled. After the excess 2-chloro-6-methylphenol is then omitted as first runnings, the substituted, benzylated phenol remains as nearly water-clear, viscous, odorless liquid, Kp 160°–165° C./0.2 Torr with n$_D^{20}$ 1.5635.
Analysis: Cl calculated: 12.3%, found: 12.11%.
Yield: 64%.

EXAMPLE 9

2-chloro-6-methyl-4-(4'-isopropylbenzyl)-phenol 85.8 g (0.6 mol) 2-chloro-6-methylphenol and 33.8 g (0.2 mol) 4-isopropylbenzyl chloride, dissolved in 160 ml chloroform, are reacted with 18 g water-free zinc chloride. At a bath temperature of 60° C. the reaction mixture is stirred 5–6 h, and then washed three times each with 150 ml water for the purpose of removing excess zinc chloride, dried across sodium sulfate and subjected to a driving-off of the solvent chloroform in a vacuum.

Purification of the so-produced substituted benzylphenol follows through distillation under vacuum.

The excess portion of 2-chloro-6-methylphenol distills over as first fraction. At 146° C. to 150° C./0.2 Torr the desired 2-chloro-6-methyl-4-(4'-isopropylbenzyl)-phenol distills off as a nearly colorless and odorless substance with n$_D^{20}$ 1.5719. Upon standing longer the substance begins to crystallize.

Analysis: Cl calculated: 12.9%, found: 13.14%.
Yield: 82.5% of theoretical amount.

EXAMPLE 10

2-chloro-6-methyl-4-(3',4'-dichlorobenzyl)-phenol 90.4 g (0.63 mol) 2-chloro-6-methylphenol are brought to reaction with 149.4 g (0.765 mol) 3,4-dichlorobenzylchloride and 2.4 g water-free, finely mortared ZnCL$_2$ without solvent. After stirring 5–6 h at 60° C. the reaction mixture is subsequently worked up by washing three times, each with 100 ml water.

Then follows vacuum distillation for purification of the 2-chloro-6-methyl-4-(3',4'-dichlorobenzyl)-phenol.
Kp 168°–169.5° C./0.16 Torr This phenol derivative crystallizes after the distillation from 106°–107° C.

Cl calculated: 35.27%, found: 35.20%, 35.08%.
Yield 24.9% of theoretical amount.

EXAMPLE 11

2-chloro-6-methyl-4-(4'-chlorobenzyl)-phenol 178.1 g (1.25 mol) 2-chloro-6-methylphenol and 80.5 g (0.5 mol) 4-chlorobenzyl chloride are dissolved in 300 ml dry chloroform. 40 g water-free, finely mortared ZnCl$_2$ are subsequentlyadded.

The Friedel-Crafts alkylation proceeds to the extent of a visible HCl development.

The reaction mixture is stirred 5–6 h at 60° C., subsequently washed three times each with 250 ml water, after which the solvent chloroform is distilled off under normal pressure.

The purification of the 2-chloro-6-methyl-4-(4'-chlorobenzyl)-phenol follows by vacuum distillation; it distills over with Kp 135°–138° C./0.02 Torr as a somewhat yellow-green colored oily, colorless liquid.
n$_D^{20}$ 1.5990.

Cl calculated: 26.54%, found: 25.53%, 25.48%.
Yield: 47.3% of theoretical amount.

EXAMPLE 12

4-chloro-2-methyl-6-(4'-tert. butylbenzyl)-phenol 106.5 g (0.75 mol) 4-chloro-2-methylphenol and 45.67 g (0.25 mol) 4-tert. butylbenzylchloride are dissolved in 200 ml chloroform, and 22.5 g water-free zinc chloride are added as Friedel-Crafts catalyst. Thereafter the reaction mixture is stirred, whereby indeed at room temperature to the start of the reaction intense gas development, i.e. intense reaction, is to be noted. Subsequently the reaction mixture is stirred at 60° C. 5-6 h and washed three times each with 200 ml water for the purpose of removing the zinc chloride. The organic phase is dried across magnesium sulfate and the chloroform is driven off in a vacuum. At 182°–185° C./0.3 Torr the 4-chloro-2-methyl-6-(4'-tert. butylbenzyl)-phenol distills over as water-clear, viscous, nearly odorless liquid.

$n_D^{20}$ 1.5672.

Analysis:

Cl calculated: 12.3%, found: 12.34%.

Yield: 64%.

EXAMPLE 13

4-chloro-2-methyl-6-(4'-isopropylbenzyl)-phenol 4-chloro-2-methylphenol is easily producible for example from 2-methylphenol (o-cresol). Proceeding from this substituted phenol, the alkylation is to be performed by means of the substituted benzylchloride, 4-isopropylbenzylchloride. 4-isopropylbenzylchloride is readily preparable by chloromethylation of cumol.

106.5 g (0.75 mol) 4-chloro-2-methylphenol and 42.25 g (0.25 mol) 4-isopropylbenzylchloride are dissolved in 200 ml chloroform, and subsequently 22.5 g water-free zinc chloride are added for the alkylation reaction. The reaction mixture is stirred 5-6 h at 60° C. and after cooling worked up as follows:

For removal of the zinc chloride the reaction mixture is washed three times, each with 200 ml water, and subsequently dried across magnesium sulfate. The solvent chloroform is removed in a vacuum, followed by a vacuum distillation for the purpose of purifying the substituted benzylphenol. The 4-chloro-2-methyl-6-(4'-isopropylbenzyl)-phenol, an oily, nearly colorless and odorless liquid, distills off at 162°–165° C./0.4 Torr.

$n_D^{20}$ 1.5752.

Analysis: Cl calculated: 12.9%, found: 12.99%.

Yield: 50.3%.

EXAMPLE 14

4-chloro-2-ethyl-6-(4'-isopropylbenzyl)-phenol

Proceeding from 2-ethylphenol, which for example is easily produced from the by-product of chloramphenicol synthesis, the 2-nitroethylbenzene, through reduction to 2-ethylaniline, diazotization and concentrating, the 4-chloro-2-ethylphenol is accessible by chlorination.

117.5 g (0.75 mol) 4-chloro-2-ethylphenol are dissolved with 42.25 g (0.25 mol) 4-isopropylbenzylchloride in 200 ml chloroform. 22.5 g water-free zinc chloride are added thereto for the alkylation reaction. Already at 30° C. a powerful reaction takes place. The entire mixture is after-stirred 5-6 h at 60° C. for completion of the alkylation. After a cooling it is subsequently washed three times each with 200 ml water, and then dried across sodium sulfate, after which the solvent chloroform is driven off.

A vacuum distillation follows for the purpose of purification of the produced substituted benzylphenol. The 4-chloro-2-ethyl-6-(4'-isopropylbenzyl)-phenol is a colorless, nearly odorless, oily liquid.

Kp 172°–176° C./0.6 Torr, $n_D^{20}$ 1.5700.

Analysis: Cl calc.: 12.3%, found: 12.75%.

Yield: 73.6% of th.

The following examples demonstrate bactericidal effect of compounds according to the present invention.

EXAMPLE 15

| Absolute Restraint of the Growth of Gram-Positive Bacteria Through Selected Compounds of the General Formula II | | |
|---|---|---|
| Compound | Toxicity* | Effective Dilution** |
| 2-bromo-6-methyl-4-benzylphenol | 1,500 | 1:64,000 |
| 2-bromo-6-ethyl-4-benzylphenol | 2,800 | 1:250,000 |
| 2-chloro-6-methyl-4-(4'-isopropyl-benzyl)-phenol | not determined | 1:250,000 |
| 2-chloro-6-methyl-4-(4'-tert. butylbenzyl)-phenol | not determined | 1:128,000 |
| Comparison | | |
| 2-chloro-6-methyl-4-benzylphenol | 1,200 | 1:128,000 |

*The toxicity in mg/kg body weight is understood as acute toxicity in white mice with subcutaneous application.

**The effective dilution of absolute restraint of growth is given in g substance 1 ml nutrient medium.

EXAMPLE 16

| Absolute Restraint of Growth of Gram-Positive Bacteria Through Chosen Compounds of the General Formula III | |
|---|---|
| Compound | Effective Dilution |
| 4-chloro-2-methyl-6-(4'-isopropylbenzyl)-phenol | 1:250,00 |
| 4-chloro-2-methyl-6-(4'-tert. butylbenzyl)-phenol | 1:250.000 |
| Comparison | |
| 2-chloro-6-methyl-4-benzylphenol | 1:128,000 |

It will be understood that each of the elements described above, or two or more together, may also find a useful application in other types of compounds and their production differing from the types described above.

While the invention has been illustrated and described as embodied in antimicrobially effective phenol derivatives and methods for their production, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

We claim:

1. Phenol derivatives of the general Formula I

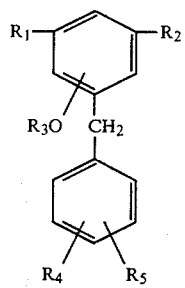

in which
- $R_1$ is bromine or chlorine,
- $R_2$ is methyl,
- $R_3$ is hydrogen, sodium, potassium, calcium, barium, ammonium, by alkyl with up to 10 C-atoms substituted ammonium, magnesium, bismuth, tin, zinc, aluminum or copper, and
- $R_4$ and $R_5$ are independently hydrogen, alkyl or alkoxy with up to 5 C-atoms, bromine or chlorine, with the proviso that in no single compound is $R_1$ chlorine, $R_2$ methyl, and $R_3$, $R_4$ and $R_5$ hydrogen.

2. Phenol derivatives of the general formula III

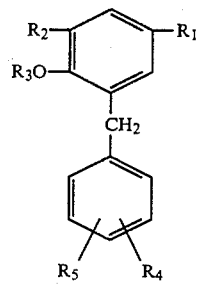

in which
- $R_1$ is bromine or chlorine,
- $R_2$ is methyl,
- $R_3$ is hydrogen, sodium, potassium, calcium, barium ammonium, by alkyl with up to 10 C-atoms substituted ammonium, magnesium bismuth, tin, zinc, aluminum or copper, and
- $R_4$ and $R_5$ are independently hydrogen, alkyl or alkoxy with up to 5 C-atoms, bromine or chlorine with the proviso that in no single compound is $R_1$ chlorine, $R_2$ methyl, and $R_3$, $R_4$ and $R_5$ hydrogen.

3. Salt of the phenol derivative of the general Formula I

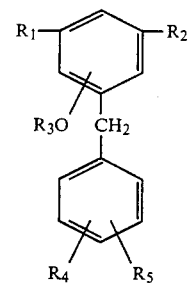

in which
- $R_1$ is bromine or chlorine,
- $R_2$ is methyl or ethyl,
- $R_3$ is sodium, potassium, calcium, barium, ammonium, ammonium substituted by alkyl with up to 10 C-atoms, magnesium, bismuth, tin, zinc, aluminum or copper, and
- $R_4$ and $R_5$ are independently hydrogen, alkyl or alkoxy with up to 5 C-atoms, bromine or chlorine.

4. Salt of the phenol derivative of the general Formula III

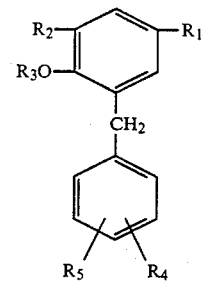

in which
- $R_1$ is bromine or chlorine,
- $R_2$ is methyl or ethyl,
- $R_3$ is sodium, potassium, calcium, barium, ammonium, ammonium substituted by alkyl with up to 10 C-atoms, magnesium, bismuth, tin, zinc, aluminum or copper, and
- $R_4$ and $R_5$ are independently hydrogen, alkyl or alkoxy with up to 5 C-atoms, bromine or chlorine.

5. Method of restraining the growth of gram-positive bacteria comprising applying to or within the locus of said bacteria bactericidally effective amounts of compounds according to claim 1.

6. Method according to claim 5, wherein said compound is applied in pharmaceutically acceptable carrier material.

* * * * *